US007800061B2

(12) United States Patent
James et al.

(10) Patent No.: US 7,800,061 B2
(45) Date of Patent: Sep. 21, 2010

(54) SUSPENSION SYSTEM AND SCANNING METHOD (75) Inventors: Kenneth James, Yarm (GB); Lee Michael Robins, Norton (GB)

(73) Assignee: Johnson Matthey PLC, London (GB)

( * ) Notice: Subject to any disclaimer, the term of this patent is extended or adjusted under 35 U.S.C. 154(b) by 294 days.

(21) Appl. No.: 12/094,695

(22) PCT Filed: Nov. 21, 2006

(86) PCT No.: PCT/GB2006/050407

§ 371 (c)(1),
(2), (4) Date: May 22, 2008

(87) PCT Pub. No.: WO2007/060481

PCT Pub. Date: May 31, 2007

(65) Prior Publication Data

US 2008/0290302 A1   Nov. 27, 2008

(30) Foreign Application Priority Data

Nov. 22, 2005   (GB) ................... 0523647.6

(51) Int. Cl.
*G01N 21/86* (2006.01)
(52) U.S. Cl. .................... 250/308; 250/360.1

(58) Field of Classification Search ............... 250/308, 250/358.1, 360.1
See application file for complete search history.

(56) References Cited

U.S. PATENT DOCUMENTS 3,602,715 A * 8/1971 McDivitt ............. 250/308

FOREIGN PATENT DOCUMENTS

| EP | 0 686 828 A1 | 12/1995 |
| GB | 1090912 | 11/1967 |
| GB | 1145332 | 3/1969 |
| JP | 57-201823 | 12/1982 |

* cited by examiner

*Primary Examiner*—Kiet T Nguyen
(74) *Attorney, Agent, or Firm*—RatnerPrestia (57) ABSTRACT A method and apparatus for performing a radiation scan of a structure involve arranging a source of penetrating radiation and a radiation detector at opposed ends of a radiation path through the structure, oriented in such a way that the source emits radiation along the path through the structure and the detector is capable of detecting the radiation after it has passed through the structure and monitoring the radiation emitted from the source that is detected by the detector. At least one continuous loop of a cable is mounted on the structure between at least two fixed locations on the structure so that the cable is movable along its length relative to the structure, and the at least one of the source of penetrating radiation and the radiation detector are fixed to the cable.

20 Claims, 5 Drawing Sheets

SUSPENSION SYSTEM AND SCANNING METHOD

CROSS-REFERENCE TO RELATED APPLICATIONS

This application is the U.S. National Phase application of PCT International Application No. PCT/GB2006/050407, filed Nov. 21, 2006, and claims priority of British Patent Application No. 0523647.6, filed Nov. 22, 2005.

FIELD OF THE INVENTION

The present invention concerns a method for scanning a large structure and a suspension system for use in such a method.

BACKGROUND OF THE INVENTION

It is known to use radiation scanning methods for the monitoring of large structures and vessels such as process vessels and storage tanks. In a typical scanning operation of a process vessel, a radioactive source located adjacent the exterior surface of the vessel is arranged to emit radiation through the vessel and a radiation detector is located adjacent a different portion of the vessel to detect radiation that has passed through the vessel. The amount of radiation passing through the vessel is an indication of the density of the material. In this way the level of the material or of more than one material within the vessel may be monitored. The method is also useful for detecting the presence of process equipment within the vessel, so that, for example, the presence of trays in a distillation column can be verified.

The method used typically requires the radiation source and the detector to be aligned along a linear path between the source and detector and moved to different locations outside the vessel whilst remaining in alignment with each other. This procedure normally requires at least two skilled operators to be present, usually at the top of the vessel. Such a procedure is therefore labour intensive and may be hazardous to the operators, particularly in bad weather. It is an object of the present invention to provide a method of scanning a structure which overcomes some of these difficulties.

SUMMARY OF THE INVENTION

According to the invention, we provide a method of carrying out a radiation scan of a structure by arranging a source of penetrating radiation and a radiation detector at opposed ends of a radiation path through the structure, oriented in such a way that the source emits radiation along the path through the structure and the detector is capable of detecting the radiation after it has passed through the structure along said path and monitoring the radiation emitted from the source that is detected by the detector; characterised in that at least one of the source of penetrating radiation and the radiation detector is fixed to a continuous loop of a cable, said cable being mounted on said structure between at least four fixed locations on said structure such that the cable is movable along the direction of its own longitudinal axis relative to the structure.

The method preferably further comprises a) mounting on said structure at least one continuous loop of a cable, said cable being mounted between at least four fixed locations on said structure and being movable along the direction of its own longitudinal axis relative to the structure, b) fixing to said cable at least one of the source of penetrating radiation and the radiation detector, c) arranging the other of said source and detector to emit radiation to or detect radiation from the source or detector that is fixed to the cable, d) monitoring the radiation received by the detector when the cable is in a first position e) moving said cable along its longitudinal axis thereby to move the source or detector fixed to the cable to a second position relative to said structure f) monitoring the radiation received by the detector in said second position.

According to a second aspect of the invention, we provide an apparatus for performing a scan of a structure comprising:

a) at least one continuous loop of a cable, said cable being mounted on said structure and being movable along the direction of its own longitudinal axis relative to the structure, b) a source of penetrating radiation mounted in a fixed position on said loop of cable so that it is movable relative to the structure with the loop and adapted to emit radiation through said structure, c) a radiation detector mounted in a fixed position on said loop of cable so that it is movable relative to the structure with the loop and adapted to receive radiation from said radiation source, and d) means for monitoring the radiation received by the detector which has been transmitted from said source along a path through the structure between said source and said detector.

BRIEF DESCRIPTION OF THE DRAWINGS

The invention will be further described by way of example only and with reference to the accompanying drawings, which are.

DETAILED DESCRIPTION OF THE INVENTION

By "cable" we mean a flexible elongate linear material which is strong enough to support a radiation source and detector and to which the radiation source and detector may be fixed. A cable is the most convenient material, typically made of steel or another suitable material, optionally provided with a protective coating. The thickness of the cable should be selected to provide sufficient strength and flexibility to support its own weight and that of the source and/or detector and pass between the fixed locations on the structure. Typically the cable is between about 1 mm and 5 mm thick. A chain may be used as an alternative to a cable. A rope or wire may also be suitable but these are less preferred.

By "continuous loop" we include any loop whether or not it includes a joining portion or joining means such as links, chains etc to close two ends of the cable to form a loop. That is to say, a suitable loop may be formed from one or more linear lengths of cable, the ends of which have been joined to form a loop. The continuous loop may incorporate the radiation source and/or detector so that the loop may comprise one or more portions of cable interrupted by the radiation source and/or detector and optionally interrupted by other apparatus, fixtures or materials.

The structure may be any of a variety of structures, for example engineering structures or, preferably, industrial vessels such as storage or process vessels. Typically the structure is of an elongated shape, e.g. cylindrical and of homogeneous cross-section along its length although other structures and shapes may be scanned with the method and apparatus of the invention.

In a preferred form of the invention, both a source and a detector are mounted on a continuous loop of cable. In a more preferred form of the invention, the source and detector are fixed to the same one continuous loop.

The source and detector define a path between them through the structure along which the radiation travels from the source and is detected by the detector. The amount of radiation absorbed or scattered by the structure is indicated by a correspondingly reduced amount of radiation impinging upon the detector. The absorption or scattering of radiation indicates a property of the material of the structure through which the radiation path has passed. In order to monitor the difference in the property of the material in different parts of the structure, the radiation is preferably detected along at least two different paths through the structure each path being defined between the source and detector. When the source and/or detector is located in a first position relative to the structure to be scanned and then moved to a second, different position then the properties of the structure may be measured along a first and second path through the structure. When the structure is a vessel, for example, and the contents of the vessel vary according to the location within the vessel, the detection of radiation along more than one path through the vessel may provide information about the contents of the vessel at each location through which the radiation path passes.

The cable loop is mounted on the structure between at least two fixed locations on the structure and is movable along the axis of the cable. In a preferred embodiment of the invention, a single cable loop is mounted on a structure to scan a portion of the structure between a first side and a second side of the structure, the portion having first and second ends. The radiation source and detector are fixed to the single cable loop such that when the cable loop is mounted on the structure, the source and detector are located at opposed ends of a desired radiation path through the portion of the structure to be scanned. The cable route passes over the surface of the structure and traverses the portion to be scanned and preferably extends beyond the two ends of the portion. In this embodiment, the cable path passes through at least four fixed locations relative to the structure, the fixed locations being: on a first external surface of the structure, a first location near a first end of the portion and a second location near an opposed second end of the portion; and on a second external surface of the structure a third location near said second end of the portion and fourth location near said opposed first end of the portion on the second surface. The cable is movable along a cable route running between said locations in the sequence first-second-third-fourth-third-second-first. By first and second surfaces of the structure we refer to two surfaces of the structure defining between them a portion of the structure through which radiation may travel from the radiation source located at or near the first surface through the structure to the detector located at or near the second surface. The cable is preferably mounted in such a way that it is spaced apart from the surface of the structure to be scanned. When the structure is cylindrical, spherical or other shape having a continuous outer surface, the first and second surfaces are portions of the continuous surface defining a path between them through which radiation may travel from the source to the detector. The path of radiation through the structure from the first to the second surface may follow a diameter or diagonal of the structure, a chord or other path.

It is greatly preferred that a radiation source and a detector are fixed to portions of the cable which move in the same direction relative to the structure so that movement of the cable moves both the source and detector the same distance in the same direction relative to the structure along the route of the cable. Preferably the movement of the source is parallel to the movement of the detector. In this way the length of the radiation path through the structure is constant over the portion of the structure to be scanned. When the movements of source and detector are not parallel or where the structure has a shape or cross section which is not constant over the length of the portion to be scanned, then it may be possible to compensate for the variation in the shape of the structure or length of the radiation path by calculating an appropriate correction factor to apply to the results, e.g. when the structure is a spherical vessel for example.

The loop is preferably mounted using a mounting means that enables the cable to move easily without undue friction. The mounting means serves to support the cable and guide it through fixed locations on the structure. This is conveniently achieved using bearings or pulley wheels although other devices may be used to achieve this function. "Barton" pulleys and blocks are suitable for this purpose and are widely available. Each fixed location may include more than one cable mounting means mounted on the structure. The cable mountings preferably mount the cable a sufficient distance away from the surface of the structure to enable the cable and attached radiation monitoring equipment to move without catching and fouling parts of the structure such as walkways, valves and pipes. The location for the cable mountings should be selected to provide a path for the cable which is relatively free of such obstacles. The cable fixings optimally include a mounting bracket which may be fixed to the structure to be scanned and upon which one or more pulleys or bearings may be mounted. The brackets or other mounting device may be permanently fixed to the structure by bolts, rivets or other mounting means. Alternatively a semi-permanent mounting arrangement may be used. A preferred semi-permanent mounting means comprises tension bands or cable ties which are adapted to embrace the structure or a part of it under sufficient tension to hold it in place and to which the cable fixings may be attached. Tension bands are especially suitable for mounting the cable fixings to a generally cylindrical process vessel such as a storage tank or reactor. Tension bands are readily available and widely used in industry for attaching lagging to vessels and pipes for example. Preferably additional cable mounting means, suitably in the form of pulleys or bearings, are provided to guide the cable between the fixed locations on the structure, e.g. from a first side to a second side of the structure.

The cable is moved in order to move the radiation source and/or detector affixed thereto. The movement of the cable may be effected manually, by mechanical means such as a winding crank or by motorised means. In order to ensure that the scan is conducted at known positions along the route of the cable, the movement of the cable is preferably measured. Such a measurement may be achieved using a linear measure, but in a preferred embodiment the cable movement is measured by moving the cable through a measuring means such as a wire-meter of the conventional type. A wire meter is a device having at least one wheel over which a wire or cable is passed in such a way that rotation of the wheel is proportional to the distance the cable has moved. The rotation of the wheel is converted to a distance which can be read out on the wire meter. As an option the cable movement may be made and measured by a combined motor and measuring device. The movement of the source and detector may be continuous or intermittent and may be in one or both directions. When continuous movement and scanning is required then it is convenient to use a motorised device for moving the cable. The device may incorporate measuring means arranged to provide an electronic signal to data processing apparatus for automated scanning.

The radiation source is mounted in a source-holder having fixing means for attaching the source holder to the cable. The fixing means may comprise a loop or eye through which the cable may pass. The source-holder is preferably of a streamlined shape to minimise the risk of fouling on the structure at preferably sized to pass though or around typical apparatus such as pipe-work, walkways and gratings associated with large structures. In a preferred form the source holder is generally cylindrical with tapered ends and of a diameter of from 10 mm to 50 mm, preferably about 20 mm in order to pass through a Kennedy grating typically found on chemical processing plant. When the radiation source is a source of ionising radiation or other potentially harmful radiation then the source holder preferably includes a shielding material shaped to minimise the emission of radiation in a direction other than towards the detector. The shielding material provides shielding for the operator and other personnel and also functions to collimate the radiation to provide a beam for shining through the structure towards the detector. More than one source may be fixed to the cable but the collimation applied to multiple sources must be carefully designed in order to avoid cross-talk.

The radiation detector comprises any detector which is capable of detecting the type of radiation emitted by the source and which can be made sufficiently compact for fixing to the cable. The detector is preferably housed within a protective housing formed from a tough material which is of a streamlined shape to minimise the risk of fouling on the structure and is preferably sized to pass though or around typical apparatus such as pipe-work, walkways and gratings of the type usually associated with large structures. The housing includes fixing means, such as a loop etc, for attaching it to the cable. In a preferred form, the detector housing is generally cylindrical with tapered ends and of a diameter of from 10 mm to 100 mm, preferably about 20-40 mm. The detector may be electrically powered. In such a case it is preferred to provide a small power source such as a battery located within the detector housing. More than one detector may be provided, particularly when more than one source is used. The housing may contain a means for transmitting signals from the detector to a remote location so that the detector signal may be monitored and processed remotely from the detector.

The signals generated by the detector in response to detected radiation are preferably passed to a data processing device for interpretation and conversion into an indication of radiation intensity received by the detector. More preferably, the data-processor may carry out a calculation of density or other property of the structure based upon the radiation received. The data processor may be arranged to receive signals from the cable measuring device in order to correlate the radiation intensity with the distance along the cable route, and thus the position on the structure, at which the radiation intensity is monitored. The data processor is normally located remotely from the detector, e.g. within a laptop computer near one part of the structure. The data processor is normally associated with display means for indicating the results of the scan. When the data processor is remote from the detector, the communication between them is preferably by wireless means in order to avoid the use of wires or cables which may become entangled with the cable loop. When a wireless communication means is provided between the detector and a remote data-processor, a power source for the communication means should normally be present. Therefore the detector housing may contain a transmitter for transmitting a signal from the detector to the data processor. As a less-preferred option, the signals generated by the detector may be stored on a data storage device located within the detector housing. The storage device may then be retrieved from the detector at intervals during or after the scan for transfer of the data to a data processing device. This option is less preferred because it does not allow for real-time monitoring of the structure.

In a preferred form the radiation comprises ionising radiation such as X-rays or, more preferably, gamma rays. Alternatively microwaves, radio waves, sound waves may be used. The radiation used is selected by the transparency of the structure to be scanned and the availability of suitable compact sources and detectors. Radiation from the visible or near-visible spectrum could be used but its use would be very limited. For scanning large solid structures such as process vessels, gamma radiation is greatly preferred. Suitable sources of gamma include $^{60}$Co and $^{137}$Cs, $^{24}$Na and $^{182}$Ta, however any gamma-emitting isotope of sufficient penetrating power could be used, and many such are already routinely used in radiation scanning. Suitable sources emit radiation at energies between about 100 and 1500 keV and suitable detectors can detect such radiation with sufficient sensitivity that the radiation detected varies according to the property of the structure to be measured. The preferred detector is a scintillation detector such as a sodium iodide crystal. This type of detector is available as a compact unit, from about 25 mm in diameter and about 40 mm in length so is suitable for mounting in the detector housing. Scintillation detectors are preferred because they are more sensitive than Geiger-Muller tubes and can therefore be used with smaller sources. A Geiger Muller tube may, of course, be used if required.

The cable and fixings may be left in place mounted on the structure when a scan has been completed in order to minimise the time required to prepare for a subsequent scan, if required. In this case, the source and preferably also the detector would normally be removed from the cable on completion of the scan in order to control exposure to the source radiation and then replaced prior to carrying out a subsequent scan.

Use of the method and apparatus of the invention allows a radiation scan of a structure or vessel to be performed by a single operator located on the ground. The operator is able to move the source or detector (and preferably both) through a desired distance during the scanning operation by moving the cable to which they are attached. When the source and detector are fixed to the same loop of cable on portions of the cable that move in the same direction relative to the structure, then the operator can move both the source and detector at the same time, maintaining the alignment between them, by moving an accessible part of the cable. This is a significant benefit in terms of the number of operators required to carry out a scan and for the safety of the operators. When the cable has been mounted on a structure or vessel it may be left in place following the scan so that set up time for subsequent scans is greatly reduced. This is of benefit for routine scanning of process vessels, for example, where periodic scans are carried out to monitor the condition of the vessel contents over a period of time.

Figure 1:
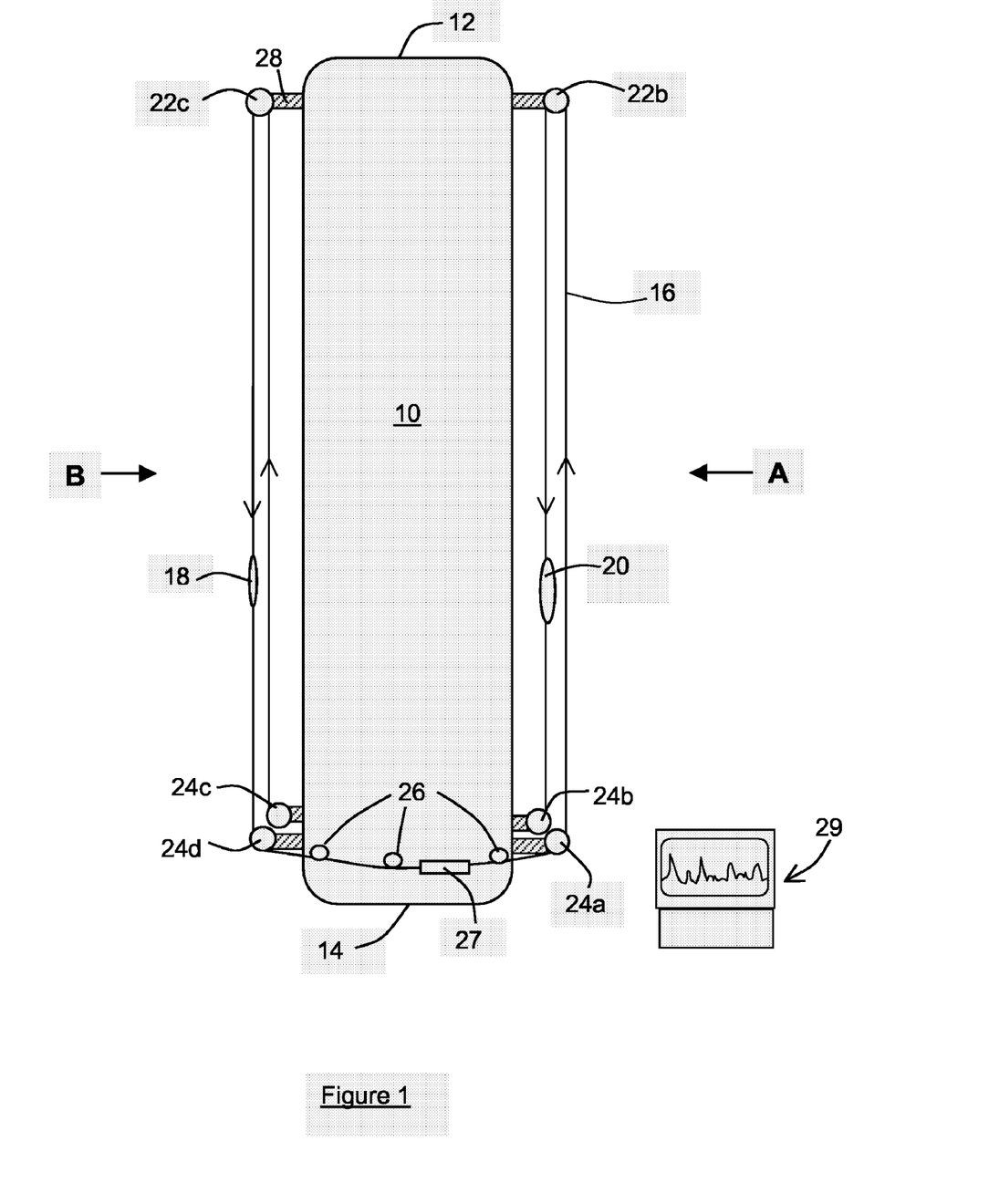
FIG. 1, a schematic perspective view of a process vessel to which apparatus of the invention have been fixed in such a way as to carry out the process of the invention.
Figure 2:
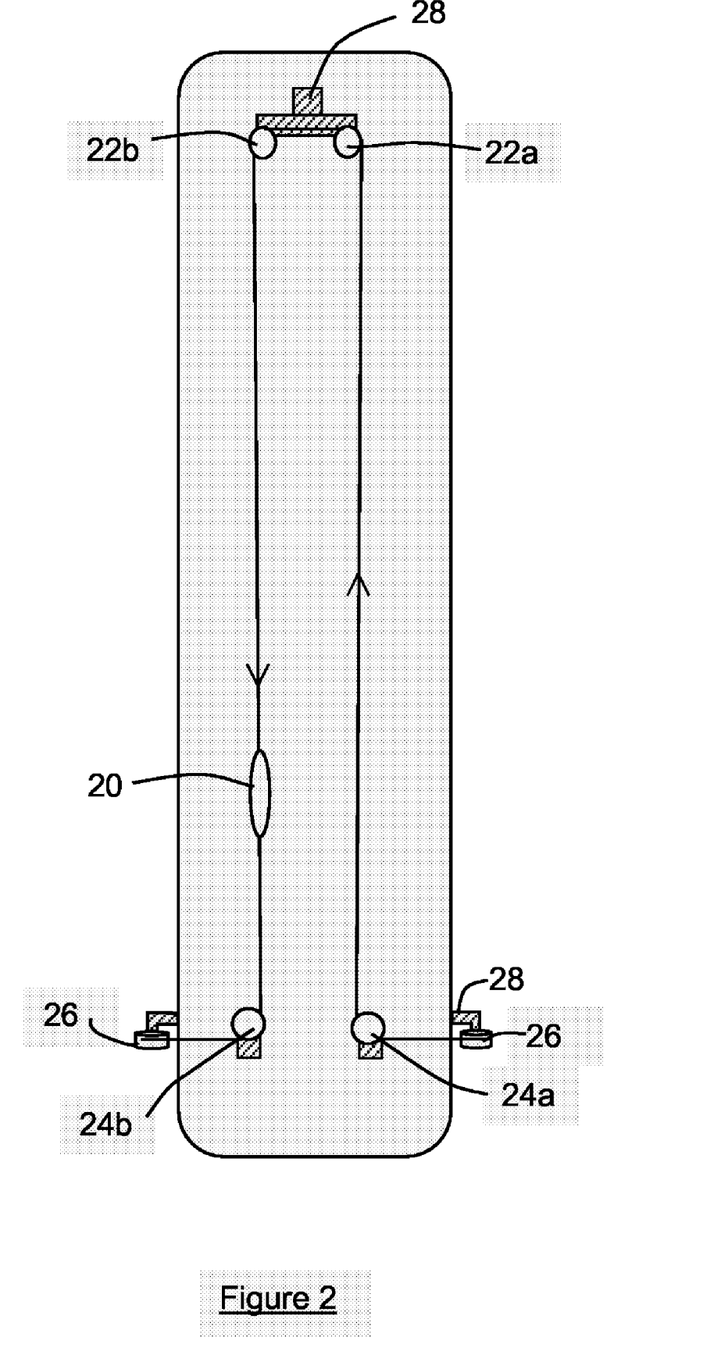
FIG. 2, a schematic perspective view of the process vessel of FIG. 1 from a viewing position 90 degrees from FIG. 1, at position A.
Figure 3:
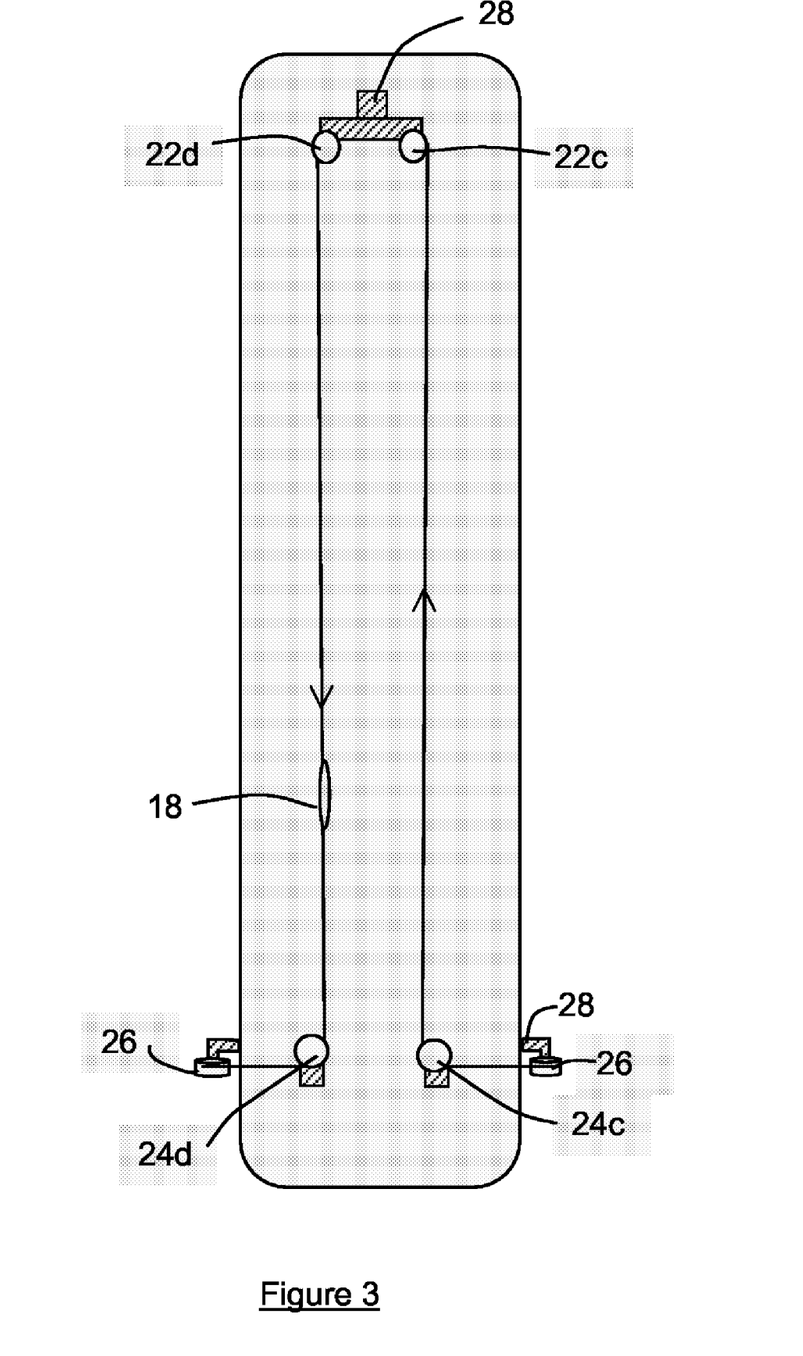
FIG. 3, a schematic perspective view of the process vessel of FIG. 1 from a viewing position 90 degrees from FIG. 1, at position B.

FIGS. 1 to 3 show a cylindrical process vessel 10 having a top end 12 and a bottom end 14. The apparatus of the invention is fixed to the process vessel. The apparatus comprises a cable 16 formed into a loop, a source holder 18 and a detector 20. The cable is a 1.2 mm diameter stainless steel cable having a breaking strength of 200 kg. The cable is supported on the process vessel by top pulleys 22, bottom pulleys 24 and guide pulleys 26. The pulleys 22-26 comprise low-friction pulley blocks mounted on brackets 28 by which the pulleys are fixed to the process vessel using steel tension bands (not shown). In this embodiment, each fixed location on the vessel through which the cable passes has a pair of pulleys. The locations are: first (pulleys 22 a&b) at the top of one side of the vessel; second (pulleys 24 a& b) at the bottom of the same side of the vessel, third (24c & d) and fourth (22c&d) at the bottom and top respectively of the opposite side of the vessel. The cable runs between two top pulleys 22a,b then down the vessel to a bottom pulley 24b, around the vessel via guide pulleys 26 to bottom pulley 24c up the vessel to top pulley 22c, across to top pulley 22d, down the vessel to bottom pulley 24d and then via guide pulleys 26 and a wire meter 27 to bottom pulley 24a then back up the vessel to top pulley 22a, forming a continuous loop. The loop may be interrupted by a join or by the detector or source holder 18, 20. The direction of movement of the cable is indicated by arrows on the drawings.

Figure 4:
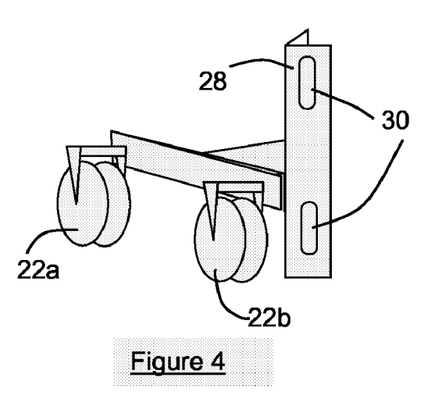
FIG. 4, a top bracket and two-pulley fixing.
Figure 5:
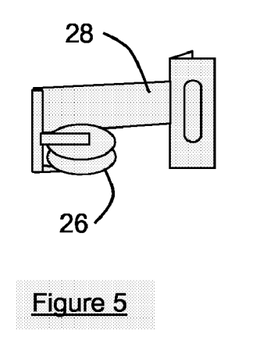
FIG. 5, a side bracket and pulley.

The pulley block and brackets are shown in more detail in FIGS. 4 & 5. The top pulleys 22 are mounted as a pair on a single bracket, for convenience. They may of course be mounted singly as an alternative. The brackets include holes 30 through which a tension band may be passed in order to fix the bracket to the process vessel. The brackets typically support the cable a short distance (about 15 cm) away from the wall of the vessel.

Figure 6:
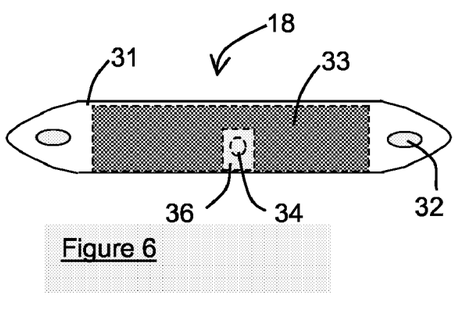
FIG. 6, a source holder.

In FIG. 6, the source holder 18 comprises a streamlined tapered cylindrical housing 30 about 20 mm in diameter and having a hole at each end by which the source holder may be fastened to the cable. An end of the cable may be fastened to each of the holes in the source holder in such a way that the source holder itself forms part of the continuous loop. Suitable fasteners include Arakawa™ fittings which allow cable to pass though in a single direction. Use of these fittings enables the position of the source to be adjusted during initial set-up of the apparatus. The source holder contains a radiation absorbing shielding material which acts to direct the radiation from the source transversely with respect to the source holder through the radiation transparent part of the source holder 36. The source 34, comprising cobalt-60, is located within a space in the shielding material. The shielding material greatly reduces the radiation emitted from the source holder upwards and downwards and so is present for the protection of operating personnel in addition to acting as a collimator for the radiation source.

Figure 7:
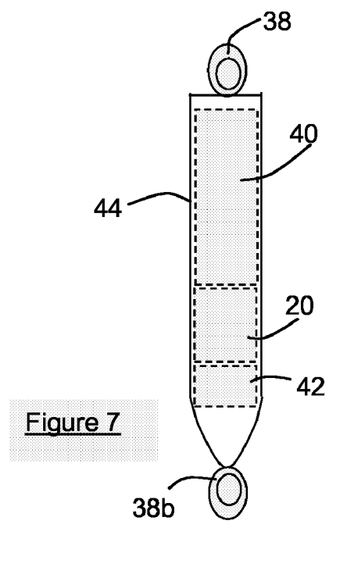
FIG. 7, a detector and detector housing

The detector 20 shown in FIG. 7 is a 50 mm (2-inch) sodium iodide crystal located within a generally cylindrical streamlined housing 44. The housing is provided with eyelets 38 through which the cable may pass of be attached. The housing also contains a battery pack 40 to provide power to the detector and to a transmitter 42 which transmits signals from the detector to a receiver, here contained within laptop computer 29.

To conduct a scan of vessel 10 using the method of the invention when the apparatus described above is in place the operator first ensures that the source 18 and detector 20 are in horizontal alignment on the cable 16 so that the detector is in the optimum position for receiving radiation emitted from the source and passing horizontally through the vessel. An initial reading of the radiation detected is recorded in that position by the data processing computer 29. Then the cable is moved through the wire meter by a measured distance to a second position, the distance and new radiation measurements being recorded in that second position. The radiation passing through the vessel may then be recorded in a number of subsequent positions by moving the cable through the wire meter by the required distance. The source and detector are both moved the same distance, being a distance equivalent to the distance moved by the cable through the wire meter each time the cable is repositioned. The source and detector therefore remain in alignment throughout the scan. When the scan is complete the brackets and pulleys may remain in place on the vessel so that set-up time is minimised if a subsequent scan is required to be carried out on the same vessel. The source and preferably also the detector would normally be removed from the cable and stored securely on completion of the scan in order to control exposure to the source radiation and then replaced prior to carrying out a subsequent scan.

Figure 8:
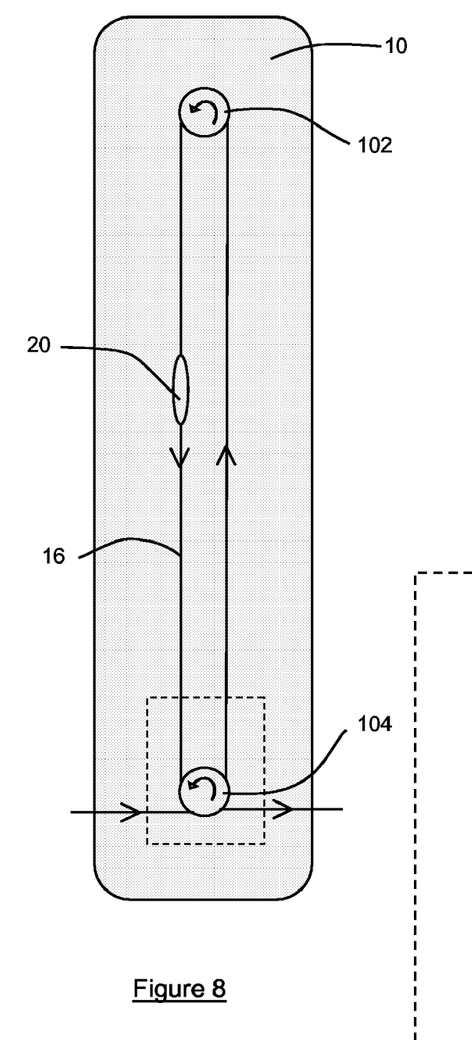
FIG. 8, a schematic view of an alternative arrangement of the apparatus of the invention.
Figure 9:
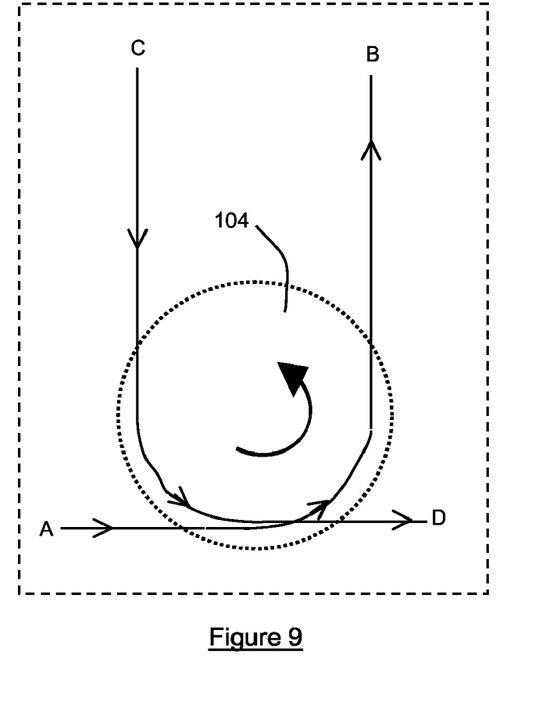
FIG. 9, an expanded view of a portion of FIG. 8.

FIGS. 8 and 9 show an alternative arrangement of pulleys to that shown in FIGS. 1-3. In FIG. 8, which shows one side of a process vessel scanning apparatus, there is a single top pulley 102 and a single bottom pulley 104. The direction of rotation of the pulleys is shown by the curved arrows. The guide pulleys around the side of the vessel have been omitted from the drawing for clarity. The portion of the drawing within the dashed box in FIG. 8 is represented in expanded form in FIG. 9 to show the route of the cable 16 around the pulley 104 more clearly. In FIG. 9, pulley 104 is shown as a dashed outline. The cable passes from the other side of the vessel through location A, partially around pulley 104 and continues through location B up to pulley wheel 102. The cable then passes over pulley 102 and continues down through location C, then partially around pulley 104 through location D as it continues around the vessel to return to the other side. The difference between this arrangement and that of FIG. 2 is that the top and bottom pulley wheels 22 *a-b* and 24 *a-b* have been replaced by single pulley wheels 102 and 104. Such an arrangement is possible if the cable route shown can be followed without one part of the cable fouling or sticking as it crosses another part of the cable. A suitable design of pulley wheel may be used to alleviate such a problem. As a further alternative, pulley wheel 104 may be replaced by two separate wheels arranged to rotate about a single axis.

The cable route shown in FIGS. 8 & 9 is functionally the same as that of FIGS. 1-3 and the method of performing the scan is the same.

The invention claimed is:

1. A method of carrying out a radiation scan of a structure comprising the steps of
   i. arranging a source of penetrating radiation and a radiation detector at opposed ends of a radiation path through the structure, said source and detector being oriented in such a way that the source emits radiation along the path through the structure and the detector is capable of detecting the radiation after it has passed through the structure along said path:

ii. monitoring the radiation emitted from the source that is detected by the detector;

wherein at least one of the source of penetrating radiation and the radiation detector is fixed to a continuous loop of a cable, said cable being mounted on said structure such that the cable is movable along the direction of its own longitudinal axis relative to the structure.

2. A method according to claim 1, wherein both the source and detector are fixed to the continuous loop of cable.

3. A method according to claim 1, wherein the cable is mounted on the structure between at least four fixed locations on the structure.

4. A method according to claim 3, wherein the four fixed locations are: on a first external surface of the structure, a first location near a first end of the portion and a second location near an opposed second end of the portion; and on a second external surface of the structure a third location near said second end of the portion and fourth location near said opposed first end of the portion on the second surface and the cable is movable along a cable route running between said locations in the sequence first-second-third-fourth-third-second-first.

5. A method according to claim 1 wherein
   a) the monitoring step comprises monitoring the radiation received by the detector when the cable is in a first position
   b) the method further comprises the step of moving said cable along its longitudinal axis thereby to move the source or detector fixed to the cable to a second position relative to said structure, and
   c) the monitoring step further comprises monitoring the radiation received by the detector in said second position.

6. A method according to claim 1, wherein the cable is moved through a measuring means.

7. A method according to claim 1, wherein said radiation source and said radiation detector are fixed to portions of the same continuous loop of cable which move in the same direction relative to the structure such that movement of the cable moves both the source and detector the same distance in the same direction relative to the structure along the route of the cable.

8. A method according to claim 1, wherein the further comprising the step of passing signals, generated by the detector in response to the radiation received, to a data processing device.

9. A method according to claim 8, wherein the signals are passed using wireless transmission means.

10. A method according to claim 1, further comprising the step of demounting the detector and/or radiation source from the cable whilst the cable is mounted on the structure.

11. An apparatus for performing a scan of a structure comprising:
    a) at least one continuous loop of a cable, said cable being mounted on said structure and being movable along its length relative to the structure,
    b) a source of penetrating radiation mounted in a fixed position on said loop so that it is movable relative to the structure with the loop and adapted to emit radiation through said structure,
    c) a radiation detector mounted in a fixed position on said loop so that it is movable relative to the structure with the loop and adapted to receive radiation from said radiation source,
    d) means for monitoring the radiation received by the detector which has been transmitted from said source through a path through the structure defined by a linear path from said source to said detector.

12. An apparatus according to claim 11, further comprising cable mounting means for mounting the cable on said structure such that it is movable along the direction of its own longitudinal axis relative to the structure to pass through or over at least four fixed locations which are:
    on a first external surface of the structure, a first location near a first end of the portion and a second location near an opposed second end of the portion; and on a second external surface of the structure a third location near said second end of the portion and fourth location near said opposed first end of the portion on the second surface and the cable is movable along a cable route running between said locations in the sequence first-second-third-fourth-third-second-first.

13. An apparatus according to claim 12, wherein said cable mounting means comprises at least one pulley wheel mounted on said structure at each location, adapted to support the cable and to allow the cable to move through or around each location.

14. An apparatus according to claim 11, wherein the radiation source is mounted in a source-holder having fixing means for attaching the source holder to the cable and shielding material which is impermeable to the radiation emitted by the source and is shaped to provide shielding for the operator and other personnel and to collimate the radiation to provide a beam for shining through the structure towards the detector.

15. An apparatus according to claim 11 wherein the radiation detector is housed within a protective housing formed from a tough material, said housing having fixing means for attaching it to the cable.

16. An apparatus according to claim 15, wherein said housing contains a power source.

17. An apparatus according to claim 15, wherein said housing contains a means for transmitting signals from the detector to a remote location.

18. An apparatus according to claim 11, wherein said monitoring means includes data processing means which is adapted to calculate a property of the structure from the data received from the detector.

19. An apparatus according to claim 11, further comprising a cable measuring means.

20. An apparatus according to claim 11, further comprising a mechanical means for moving the cable.

* * * * *

UNITED STATES PATENT AND TRADEMARK OFFICE
CERTIFICATE OF CORRECTION

| | | |
|---|---|---|
| PATENT NO. | : 7,800,061 B2 | Page 1 of 1 |
| APPLICATION NO. | : 12/094695 | |
| DATED | : September 21, 2010 | |
| INVENTOR(S) | : Kenneth James et al. | |

It is certified that error appears in the above-identified patent and that said Letters Patent is hereby corrected as shown below:

At column 9, line 43:

"A method according to claim 1 wherein the further"

should read:

--A method according to claim 1 further--.

Signed and Sealed this
Eleventh Day of January, 2011

David J. Kappos
*Director of the United States Patent and Trademark Office*